(12) United States Patent
Donovan

(10) Patent No.: US 7,704,524 B2
(45) Date of Patent: Apr. 27, 2010

(54) TRANSDERMAL BOTULINUM TOXIN ADMINISTRATION FOR THE TREATMENT OF SPASTIC MUSCLE PAIN

(75) Inventor: Stephen Donovan, Capistrano Beach, CA (US)

(73) Assignee: Allergan, Inc., Irvine, CA (US)

( * ) Notice: Subject to any disclaimer, the term of this patent is extended or adjusted under 35 U.S.C. 154(b) by 302 days.

(21) Appl. No.: 11/159,511

(22) Filed: Jun. 22, 2005

(65) Prior Publication Data

US 2006/0188525 A1    Aug. 24, 2006

Related U.S. Application Data

(62) Division of application No. 10/675,172, filed on Sep. 29, 2003, which is a division of application No. 10/194,805, filed on Jul. 11, 2002.

(51) Int. Cl.
*A61K 9/70* (2006.01)
*A61K 39/02* (2006.01)
*A61K 39/08* (2006.01)
*A61K 39/38* (2006.01)
*A61K 38/00* (2006.01)

(52) U.S. Cl. .............. 424/449; 424/236.1; 424/239.1; 424/247.1; 424/184.1; 514/2

(58) Field of Classification Search .............. None
See application file for complete search history.

(56) References Cited

U.S. PATENT DOCUMENTS

| | | | |
|---|---|---|---|
| 5,587,396 A * | 12/1996 | Smith | 514/557 |
| 6,087,327 A | 7/2000 | Pearce et al. | |
| 6,190,315 B1 | 2/2001 | Kost et al. | |
| 6,234,990 B1 | 5/2001 | Rowe et al. | |
| 6,491,657 B2 | 12/2002 | Rowe et al. | |
| 6,939,852 B2 * | 9/2005 | Graham | 514/12 |
| 2003/0157140 A1 | 8/2003 | Takada | 424/405 |

OTHER PUBLICATIONS

Wissel (Journal of Pain and Symptom Management, vol. 20, No. 1, Jul. 2000).*
Mitragotri et al (Science, vol. 269, Aug. 11, 1995).*
Bauerova et al (European Journal of Drug Metabolism and Pharmacokinetics, 2001, vol. 26, No. 1/2, p. 85-94).*
Barry (European Journal of Pharmaceutical Sciences 14(2001), 101-114).*

* cited by examiner

*Primary Examiner*—Vanessa L. Ford
(74) *Attorney, Agent, or Firm*—Claude L. Nassif; Debra Condino

(57) ABSTRACT

Pharmaceutical compositions for transdermal administration of neurotoxins to a patient include a neurotoxin, such as a botulinum toxin, and an enhancing agent that facilitates absorption of the neurotoxin through the skin of the patient and does not eliminate the bioactivity associated with the neurotoxin. The pharmaceutical compositions are topically applied on a patient, and may be provided in a transdermal patch.

14 Claims, No Drawings

TRANSDERMAL BOTULINUM TOXIN ADMINISTRATION FOR THE TREATMENT OF SPASTIC MUSCLE PAIN

CROSS REFERENCE

This application is a divisional of pending application Ser. No. 10/675,172; filed Sep. 29, 2003; which is a divisional of pending application Ser. No. 10/194,805; filed Jul. 11, 2002.

The present invention relates to pharmaceutical compositions containing neurotoxins. In particular, the present invention relates to compositions containing clostridial neurotoxins, such as botulinum toxin, for transdermal topical administration to patients.

BACKGROUND

Botulinum Toxin

The genus *Clostridium* has more than one hundred and twenty seven species, grouped according to their morphology and functions. The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified neurotoxin complex)[1] is a $LD_{50}$ in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63-84 (chapter 4) of Natural Toxins II, edited by B. R. Singh et al., Plenum Press, New York (1976) (where the stated $LD_{50}$ of botulinum toxin type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each.

Seven botulinum neurotoxins have been characterized, these being respectively botulinum neurotoxin serotypes A, B, $C_1$, D, E, F and G each of which is distinguished by neutralization with type-specific antibodies. The different serotypes of botulinum toxin can vary in the animal species that they affect and in the severity and duration of the paralysis they evoke. Botulinum toxin apparently binds with high affinity to cholinergic motor neurons, is translocated into the neuron and blocks the release of acetylcholine.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype $C_1$ was originally thought to cleave syntaxin, but was found to cleave syntaxin and SNAP-25. Each of the botulinum toxins specifically cleaves a different bond, except botulinum toxin type B (and tetanus toxin) which cleave the same bond.

Botulinum toxins have been used in clinical settings for the treatment of neuromuscular disorders characterized by hyperactive skeletal muscles. A botulinum toxin type A complex (BOTOX®) has been approved by the U.S. Food and Drug Administration for the treatment of blepharospasm, strabismus and hemifacial spasm, cervical dystonia and treatment of glabellar wrinkles. A type B botulinum toxin (MYOBLOC™) has also been approved by the FDA for the treatment of cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within a day or a few hours after injection. The typical duration of symptomatic relief from a single intramuscular injection of botulinum toxin type A averages about three to four months.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. *Biochem, J* 1;339 (pt 1):159-65:1999, and *Mov Disord,* 10(3):376:1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain,* J Neurochem 51(2); 522-527:1988) CGRP, substance P and glutamate (Sanchez-Prieto, J., et al., *Botulinum Toxin A Blocks Glutamate Exocytosis From Guinea Pig Cerebral Cortical Synaptosomes,* Eur J. Biochem 165;675-681:1897. Thus, when adequate concentrations are used, stimulus-evoked release of most neurotransmitters is blocked by botulinum toxin. See e.g. Pearce, L. B., *Pharmacologic Characterization of Botulinum Toxin For Basic Science and Medicine,* Toxicon 35(9);1373-1412 at 1393; Bigalke H., et al., *Botulinum A Neurotoxin Inhibits Non-Cholinergic Synaptic Transmission in Mouse Spinal Cord Neurons in Culture,* Brain Research 360;318-324: 1985; Habermann E., *Inhibition by Tetanus and Botulinum A Toxin of the release of [$^3$H]Noradrenaline and [$^3$H]GABA From Rat Brain Homogenate,* Experientia 44; 224-226:1988, Bigalke H., et al., *Tetanus Toxin and Botulinum A Toxin Inhibit Release and Uptake of Various Transmitters, as Studied with Particulate Preparations From Rat Brain and Spinal Cord,* Naunyn-Schmiedeberg's Arch Pharmacol 316; 244-251:1981, and; Jankovic J. et al., *Therapy With Botulinum Toxin,* Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A.

High quality crystalline botulinum toxin type A can be produced from the Hall A strain of *Clostridium botulinum* with characteristics of $\geq 3\times10^7$ U/mg, an $A_{260}/A_{278}$ of less than 0.60 and a distinct pattern of banding on gel electrophoresis. The known Shantz process can be used to obtain crystalline botulinum toxin type A, as set forth in Shantz, E. J., et al, *Properties and use of Botulinum toxin and Other Microbial Neurotoxins in Medicine,* Microbiol Rev. 56; 80-99:1992. Generally, the botulinum toxin type A complex can be isolated and purified from an anaerobic fermentation by cultivating *Clostridium botulinum* type A in a suitable medium. The known process can also be used, upon separation out of the non-toxin proteins to obtain pure botulinum toxins, such as for example: purified botulinum toxin type A with an approximately 150 kD molecular weight with a specific potency of 1-2×10$^8$ LD$_{50}$ U/mg or greater; purified botulinum toxin type B with an approximately 156 kD molecular weight with a specific potency of 1-2×10$^8$ LD$_{50}$ U/mg or greater, and; purified botulinum toxin type F with an approximately 155 kD molecular weight with a specific potency of 1-2×10$^7$ LD$_{50}$ U/mg or greater.

Botulinum toxins and/or botulinum toxin complexes can be obtained from Allergan Inc (Irvine, Calif.), Ipsen Beaufour (France), Elan Pharmaceuticals (Ireland), List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo.

Though somewhat labile, pure botulinum toxin can be used to prepare a pharmaceutical composition and like the botulinum toxin complexes, such as the toxin type A complex, is susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the botulinum toxins (which are intracellular peptidases) is dependent, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can be stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about four weeks. *Dermatol Surg* 1996 January; 22(1):39-43.

It has been reported that botulinum toxin type A has been used in clinical settings as follows:

(1) about 75-125 units of BOTOX® per intramuscular injection (multiple muscles) to treat cervical dystonia;

(2) 5-10 units of BOTOX® per intramuscular injection to treat glabellar lines (brow furrows) (5 units injected intramuscularly into the procerus muscle and 10 units injected intramuscularly into each corrugator supercilii muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U (b) flexor digitorum sublimus: 7.5 U to 30 U (c) flexor carpi ulnaris: 10 U to 40 U (d) flexor carpi radialis: 15 U to 60 U (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

Additionally, intramuscular botulinum toxin has been used in the treatment of tremor in patients with Parkinson's disease, although it has been reported that results have not been impressive. Marjama-Jyons, J., et al., *Tremor-Predominant Parkinson's Disease*, Drugs & Aging 16(4); 273-278:2000.

It is known that botulinum toxin type A can have an efficacy for up to 12 months (*European J. Neurology* 6 (Supp 4): S111-S1150:1999), and in some circumstances for as long as 27 months. The *Laryngoscope* 109:1344-1346: 1999. However, the usual duration of an intramuscular injection of Botox® is typically about 3 to 4 months. The success of botulinum toxin type A to treat a variety of clinical conditions has led to interest in other botulinum toxin serotypes. See e.g. *Eur J Neurol* 1999 November; 6(Suppl 4):S3-S 10.

In addition to having pharmacologic actions at the peripheral location, botulinum toxins may also have inhibitory effects in the central nervous system. Work by Weigand et al, *Nauny-Schmiedeberg's Arch. Pharmacol.* 1976; 292, 161-165, and Habermann, *Nauny-Schmiedeberg's Arch. Pharmacol.* 1974; 281, 47-56 showed that botulinum toxin is able to ascend to the spinal area by retrograde transport. As such, a botulinum toxin injected at a peripheral location, for example intramuscularly, may be retrograde transported to the spinal cord.

U.S. Pat. No. 5,989,545 discloses that a modified clostridial neurotoxin or fragment thereof, preferably a botulinum toxin, chemically conjugated or recombinantly fused to a particular targeting moiety can be used to treat pain by administration of the agent to the spinal cord.

Botulinum toxin is most frequently administered as a therapeutic agent by injecting a composition containing botulinum toxin into a patient using a needle or syringe. However, other modes of administration have been considered for botulinum toxins as well as botulinum toxins coupled with non-botulinum toxin receptor legends. Some modes of administration include topical application of botulinum toxin (e.g., see U.S. Pat. No. 6,063,768; U.S. Pat. No. 5,670,484; and German Patent Publication DE 198 52 981). German Patent Publication DE 198 52 981 discloses a composition containing botulinum toxin type A and a 50% dimethyl sulphoxide (DMSO) solution for the treatment of hyperhydrosis. Although DE 198 52 981 discusses that botulinum toxin may be used to treat hyperhydrosis by being topically applied to the skin, it is unclear whether the botulinum toxin permeated through the epidermis of the person, or if the effects were mediated by botulinum toxin passing through pores of the sweat glands. In any case, although DE 198 52 981 discloses that topical administration of botulinum toxin in a DMSO solution can be used to treat hyperhydrosis, compositions containing DMSO are not desirable because DMSO can irritate the skin. In addition, although U.S. Pat. No. 5,670,484 discloses topical application of botulinum toxin to treat skin lesions, it does riot disclose a composition containing botulinum toxin and an enhancing agent, as described herein. Furthermore, U.S. Pat. No. 5,670,484 only discloses that topical administration of botulinum toxin may inhibit cell proliferation. It is silent to topical application of botulinum toxin to treat disorders associated with neurosecretion of intracellular molecules. See also WO 00/15245 and Grusser Von O-J., *Die ersten systematischen Beschreibungen und tierexperimentellen Untersuchungen des Botulismus*, Sud-hoffa Archiv (1986), 70(2), 167-186.

Transdermal Delivery

Human skin comprises the dermis and the epidermis. The epidermis has several layers of tissue, namely, stratum corneum, stratum lucidum, stratum granulosum, stratum spinosum, and stratum basale (identified in order from the outer surface of the skin inward). The stratum corneum presents the most significant hurdle in transdermal delivery of medications. The stratum corneum is typically about 10-15 μm thick, and it consists of flattened, keratised cells (corneocytes) arranged in several layers. The intercellular space between the corneocytes is filled with lipidic structures, and may play an important role in the permeation of substances through skin (Bauerova et al., *Chemical enhancers for transdermal drug transport*, European Journal of Drug Metabolism and Pharmacokinetics, 2001, 26(1/2): 85-94). The rest of the epidermis below the stratum corneum is approximately 150 μm thick. The dermis is about 1-2 mm thick and is located below the epidermis. The dermis is innervated by various capillaries as well as neuronal processes.

Transdermal administration of pharmaceuticals has been the subject of research in attempt to provide an alternative route of administration of medications without undesirable consequences associated with injections and oral delivery. For example, needles often cause localized pain, and potentially exposes patients receiving injections to blood borne diseases. Oral administration suffers from poor bioavailability of medications due to the extremely acidic environment of the patient's stomach. Transdermal administration techniques attempt to overcome these shortcomings by providing non-invasive administration of pharmaceuticals. It is desirable with transdermal administration to reduce damage to a patient's skin. Thus, transdermal administration of medication may reduce or eliminate pain associated with injections, reduce the likelihood of blood contamination, and improve the bioavailability of drugs once they are incorporated systemically.

Attempts at transdermal administration of medication have attempted to improve the permeability of the stratum corneum. Most attempts of transdermal therapy are directed at administering pharmaceutical agents that are incorporated into a patient's circulatory system, and thus are systemically administered through the skin. Some attempts have included using chemical enhancing agents that increase the permeability of molecules through the skin. Some attempts have included using mechanical apparatus to bypass or ablate portions of the stratum corneum. In addition, attempts have included use of ultrasound or iontophoresis to facilitate the permeation of pharmaceuticals through the skin. As indicated above, the goal of these therapeutic methods is to deliver a pharmaceutical agent, typically a small molecule, through the skin so that an agent may pass to the capillary bed in the dermis where the agent may be systemically incorporated into the patient to achieve a therapeutic effect.

Although small molecules have been a major focus of transdermal administration techniques, it is important to note that it appears that large molecules, such as polypeptides, and protein complexes, are also amenable to transdermal administration. Erythropoietin, which is about 46 kD, has also been successfully transdermally administered (Mitragotri et al., *Ultrasound-mediated transdermal protein delivery*, Science, 1995, 269: 850-853; U.S. Pat. Nos. 5,814,599; and 6,002, 961).

What is needed therefore are pharmaceutical compositions or formulations containing therapeutically effective amounts of neurotoxins which enable the neurotoxin to permeate the skin of a patient and retain the neurotoxin's bioactivity to cause a therapeutic effect without undesirable pain associated with the administration of the neurotoxin.

SUMMARY

The present invention addresses this need and provides pharmaceutical compositions comprising a neurotoxin, which are able to be transdermally administered. The compositions of the present invention may be used to deliver the neurotoxin to a subdermal structure, such as an subdermal muscle, a subdermal sweat gland, or a subdermal sensory neuron. Thus, the composition disclosed herein may be used to effectively treat neuromuscular disorders associated with spastic muscles, treat sympathetic neuronal disorders, such as disorders associated with hyperactive sweat glands, or to reduce inflammation or pain associated with inflammation, and thus, the neurotoxin may be used as an analgesic.

The following definitions apply herein:

"About" means approximately or nearly and in the context of a numerical value or range set forth herein means ±10% of the numerical value or range recited or claimed.

"Local administration" means direct administration of a pharmaceutical at or to the vicinity of a site on or within an animal body, at which site a biological effect of the pharmaceutical is desired. Local administration excludes systemic routes of administration, such as intravenous or oral administration. Topical administration is a type of local administration in which a pharmaceutical agent is applied to a person's skin. Topical administration of a neurotoxin, such as botulinum toxin, excludes systemic administration of the neurotoxin. In other words, and unlike conventional therapeutic transdermal methods, topical administration of botulinum toxin does not result in significant amounts, such as the majority of, the neurotoxin passing into the circulatory system of the patient.

"Neurotoxin" means a biologically active molecule with a specific affinity for a neuronal cell surface receptor. Neurotoxin includes Clostridial toxins both as pure toxin and as complexed with one to more non-toxin, toxin associated proteins.

"Stabilized botulinum toxin" means a botulinum toxin that is still biologically active or that still is capable of binding to a target cell so that the botulinum toxin can effectively reduce or prevent exocytosis of intracellular molecules, such as neurotransmitters or peptides, from the cell to which the botulinum toxin is bound. Stabilized botulinum toxins are not cytotoxic.

"Enhancing agent" refers to an agent that enhances the permeability of a patient's skin so that botulinum toxin can be absorbed by the skin to achieve a therapeutic effect. In reference to the disclosure herein, enhancing agent specifically excludes dimethylsulfoxide (DMSO) or a combination of pluronic lecithin organizer (PLO) and DMSO. An enhancing agent may include, and is not limited to; alcohols, such as short chain alcohols, long chain alcohols, or polyalcohols; amines and amides, such as urea, amino acids or their esters, amides, AZONE®, derivatives of AZONE®, pyrrolidones, or derivatives of pyrrolidones; terpenes and derivatives of terpenes; fatty acids and their esters; macrocyclic compounds; tensides; or sulfoxides other than dimethylsulfoxide, such as, decylmethylsulfoxide; liposomes; transfersomes; lecithin vesicles; ethosomes; water; surfactants, such as anionic, cationic, and nonionic surfactants; polyols; and essential oils.

A suitable neurotoxin used in the pharmaceutical compositions disclosed herein may be a neurotoxin made by a bacterium, for example, the neurotoxin may be made from a *Clostridium botulinum, Clostridium butyricum,* or *Clostridium beratti.* In certain embodiments of the invention, the composition may contain botulinum toxin, which may be a botulinum toxin type A, type B, type $C_1$, type D, type E, type F, or type G. The botulinum toxin is present in the composition in an amount that results in between about $10^{-3}$ U/kg and about 10 U/kg of botulinum toxin permeating through the skin. The composition may contain an amount of botulinum toxin that causes a therapeutic effect to persist for between about 1 month and 5 years.

Other neurotoxins include recombinantly produced neurotoxins, such as botulinum toxins produced by *E. coli*. In addition or alternatively, the neurotoxin can be a modified neurotoxin, that is a neurotoxin which has at least one of its amino acids deleted, modified or replaced, as compared to a native or the modified neurotoxin can be a recombinant produced neurotoxin or a derivative or fragment thereof. The neurotoxins are still able to inhibit neurotransmitter release.

The composition containing a neurotoxin, as disclosed herein, is topically administered to a patient. Because the neurotoxin is topically administered the composition is preferably applied at or near a site that is painful or is moist from sweating. For example, if a spastic muscle is causing pain, the composition may be applied to the skin above the spastic muscle to chemodenervate the underlying spastic muscle. Or, if a particular site is inflamed, such as caused by neuronal release of substance P or calcitonin gene related peptide (CGRP), the composition may be administered at the inflammation site. In addition, if a person's sweat glands are excessively secreting fluid, the composition may be applied in proximity of the sweaty area to reduce the neuronal innervation of the sweat glands. For example, the composition may be applied to one or more arm pits, palms, or any other sweaty structure.

I have surprisingly found that a botulinum toxin, such as botulinum toxin type A, can be transdermally administered to alleviate disorders experienced by a human patient. The botulinum toxin used is administered in an amount so that between about $10^{-3}$ U/kg and 10 U/kg pass through a patient's skin. Preferably, the botulinum toxin is present in an amount so that between about $10^{-2}$ U/kg and about 1 U/kg are transdermally pass through the patient's skin. More preferably, the botulinum toxin is present in an amount so that between about $10^{-1}$ U/kg and about 1 U/kg pass through the patient's skin. Most preferably, the botulinum toxin is present in an amount so that between about 0.1 unit and about 5 units pass through the patient's skin to a subdermal target. Significantly, the therapeutic effects of the toxin in the composition can persist for between about 2 months to about 6 months when administration is of aqueous solution of the neurotoxin, and for up to about five years when the neurotoxin is administered in a composition that retains the toxin and slowly releases the toxin after it has passed through the skin. See e.g. U.S. Pat. No. 6,312,708.

Advantageously, I have discovered that by topically applying compositions containing botulinum toxin, potential complications, such as systemic toxicity or botulism poisoning, are avoided even upon administration of relatively high dosages since the stratum corneum of the skin still retains some impermeability. Thus, dosages of botulinum toxin (including types A, B, C, D, E, F, or G) can range from as low as about 1 unit to as high as about 20,000 units, without fear of adverse side effects that may threaten the patient. The particular dosages may vary depending on the condition being treated, and the particular enhancing agent and therapeutic regime being utilized. For example, treatment of subdermal, hyperactive muscles may require high dosages (e.g., 1000 units to 20,000 units) of botulinum toxin topically applied in a composition containing an enhancing agent. In comparison, treatment of neurogenic inflammation or hyperactive sweat glands may require relatively small topical dosages (e.g. about 1 unit to about 1,000 units) of botulinum toxin.

An embodiment of the present invention can be a pharmaceutical composition comprising a stabilized botulinum toxin and at least one enhancing agent for facilitating transdermal delivery of the botulinum toxin into a human patient by enhancing the permeability of the patient's skin. The botulinum toxin can be selected from the group consisting of botulinum toxin types A, B, $C_1$, D, E, F and G, a pure or purified (i.e. about 150 kD) botulinum toxin, as well as a native or recombinantly made botulinum toxin. The composition can comprise between about 1 units to about 20,000 units of the botulinum toxin, and the composition can comprises an amount of botulinum toxin sufficient to achieve a therapeutic effect lasting between 1 month and 5 years.

Notably, the enhancing agent can be an alcohol, such as a polyalcohol. Alternately, the enhancing agent can comprise a transfersome. Additionally, the composition can comprise a plurality of enhancing agents.

A detailed embodiment of the present invention can comprise a pharmaceutical composition in a transdermal patch, including a stabilized botulinum toxin that permeates through a human patient's skin without permeating in significant amount through a blood vessel when the botulinum toxin interacts with an enhancing agent provided in the transdermal patch to cause a therapeutic effect of a disorder associated with exocytosis of a molecule from a cell. "Without permeating in significant amount" means that less than 25% and preferably less than 5% of the botulinum toxin present in the pharmaceutical composition permeates into a blood vessel upon application of the transdermal patch The botulinum toxin in the composition can be provided in a dry state in the transdermal patch before the patch is applied to the patient's skin. The botulinum toxin can be mixed with the enhancing agent after the transdermal patch is applied to the patient's skin. Thus, the botulinum toxin can mix with an enhancing agent that is applied to the patient's skin before the transdermal patch is applied to the patient's skin.

A further embodiment of the present invention includes a transdermal patch, comprising a pharmaceutical composition, which comprises a stabilized botulinum toxin; and an enhancing agent that facilitates transdermal administration of the botulinum toxin in a bioactive form to a subdermal target site of a human patient without being administered to the patient's circulatory system; and an adhesive disposed on one side of the transdermal patch to removably secure the patch to the patient's skin. The adhesive can be is disposed around a depot containing the pharmaceutical composition.

The transdermal patch can further comprise a plurality of needles extending from one side of the patch that is applied to the skin, wherein the needles extend from the patch to project through the stratum corneum of the skin without rupturing a blood vessel. The botulinum toxin can be provided in a depot in the patch so that pressure applied to the patch causes botulinum toxin to be directed through the needles and under the stratum corneum. Furthermore, the botulinum toxin can be provided in a dry state in a plurality of wells, each of the wells covered by a membrane that is dissolvable with a fluid, and wherein the enhancing agent mixes with the botulinum toxin as the membrane over a well dissolves so that the absorption of the botulinum toxin is enhanced.

The present invention also encompasses a method of reducing neurotransmitter release in a subdermal structure of a patient, the method comprising the steps of non-chemically disrupting the stratum corneum of the patient's skin to reduce impermeability of the stratum corneum; and applying botulinum toxin to the skin of the patient in an area that has had the stratum corneum disrupted in the first step. The stratum corneum can be disrupted by abrasively removing the stratum corneum. Thus, the stratum corneum can be disrupted by applying an adhesive material to the patient's skin, and removing the adhesive material applied thereto. Alternately, the stratum corneum can be disrupted by applying ultrasound at a frequency between 20 kHz and less than 10 MHz at an intensity that does not permanently damage the patient's skin. Or the stratum corneum can be disrupted by passing electrical current from a first point on the patient's skin to a second point on the patient's skin. The electrical current can be passed to create a plurality of pores in the stratum corneum to enhance passage of botulinum toxin to the subdermal structures. And the botulinum toxin can be applied in a pharmaceutical composition comprising an enhancing agent for enhancing the delivery of the botulinum toxin through the skin. Thus, the botulinum toxin can be is incorporated into a transfersome.

The present invention also encompasses a method of relieving pain in a patient caused by a spastic muscle, the method comprising the steps of (a) applying ultrasound at a frequency between about 10 kHz and 1 MHz to the patient's skin overlying the spastic muscle; and (b)

applying botulinum toxin to the patient's skin that has received the ultrasound in step (a). Thus method can further comprise a step of abrasively removing portions of the stratum corneum of the patient's skin that received the ultrasound.

DESCRIPTION

The pharmaceutical composition of the present invention is capable of delivering a botulinum toxin, such as a purified 150 kD botulinum toxin molecule or as a 300-900 kD botulinum toxin complex, through a person's skin. The pharmaceutical composition contains an enhancing agent that facilitates the permeation of the botulinum toxin through the patient's skin. The pharmaceutical composition is suitable for topical administration so that the composition may penetrate the skin and transdermally denervate an underlying target structure, such as a structure innervated by a neuron. The composition may be a component of a patch that may be adhesively secured to the skin so that the toxin can pass from the patch to and through the skin to denervate an underlying target.

The present invention is based on the discovery that pharmaceutical compositions containing botulinum toxin and an enhancing agent can successfully treat several types of disorders associated with neurotransmitter release when applied to a person's skin. Examples of disorders amenable to treatment by the topical administration of the compositions set forth herein include, and are not limited to, wrinkles, such as brow furrows, headaches, such as migraine, headache pain, cervical dystonia; focal hand dystonia, neurogenic inflammation, hyperhydrosis, blepharospasm, strabismus, hemifacial spasm, eyelid disorder, cerebral palsy, focal spasticity, limb spasticity, tics, tremors, bruxism, anal fissure, fibromyalgia, dysphagia, lacrimation, and pain from muscle spasms. The topical administration of the toxin reduces the pain experienced by the patient when the toxin is administered because the patient does not need to be stuck with a needle that activates sensory pain neurons below the skin. The compositions disclosed herein provide localized relief with a botulinum toxin, without risking systemic administration of the botulinum toxin.

The neurotoxins used in accordance with the invention disclosed herein are neurotoxins that inhibit transmission of chemical or electrical signals. The neurotoxins preferably are not cytotoxic to the cells that are exposed to the neurotoxin. The neurotoxin may inhibit neurotransmission by reducing or preventing exocytosis of neurotransmitter from the neurons exposed to the neurotoxin. The suppressive effects provided by the neurotoxin should persist for a relatively long period of time, for example, for more than two months, and potentially for several years.

Examples of neurotoxins used in the compositions, include, and are not limited to, neurotoxins made from *Clostridium* bacteria, such as *Clostridium botulinum*, *Clostridium butyricum* and *Clostridium beratti*. In addition, the neurotoxins used in the methods of the invention may be a botulinum toxin selected from a group of botulinum toxin types A, B, C, D, E, F, and G. In one embodiment of the invention, the neurotoxin administered to the patient is botulinum toxin type A. Botulinum toxin type A is desirable due to its high potency in humans, ready availability, and known use for the treatment of skeletal and smooth muscle disorders when locally administered by intramuscular injection. The present invention also includes the use of (a) neurotoxins obtained or processed by bacterial culturing, toxin extraction, concentration, preservation, freeze drying, and/or reconstitution; and/or (b) modified or recombinant neurotoxins, that is neurotoxins that have had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made. These neurotoxin variants should retain the ability to inhibit neurotransmission between or among neurons, and some of these variants may provide increased durations of inhibitory effects as compared to native neurotoxins, or may provide enhanced binding specificity to the neurons exposed to the neurotoxins. These neurotoxin variants may be selected by screening the variants using conventional assays to identify neurotoxins that have the desired physiological effects of inhibiting neurotransmission.

Botulinum toxins for use according to the present invention can be stored in lyophilized, vacuum dried form in containers under vacuum pressure or as stable liquids. Prior to lyophilization the botulinum toxin can be combined with pharmaceutically acceptable excipients, stabilizers and/or carriers, such as albumin. The lyophilized material can be reconstituted with saline or water to create a solution or composition containing the botulinum toxin to be administered to the patient.

Although the composition may only contain a single type of neurotoxin, such as botulinum toxin type A, as the active ingredient to suppress neurotransmission, other therapeutic compositions may include two or more types of neurotoxins, which may provide enhanced therapeutic effects of the disorders. For example, a composition administered to a patient may include botulinum toxin type A and botulinum toxin type B. Administering a single composition containing two different neurotoxins may permit the effective concentration of each of the neurotoxins to be lower than if a single neurotoxin is administered to the patient while still achieving the desired therapeutic effects.

An enhancing agent used in combination with the neurotoxin in the pharmaceutical composition may be any non-DMSO based enhancing anent that enhances the permeability of the skin so that bioactive neurotoxin may act at a desired target structure. The enhancing agent preferably does not injure the skin, and more preferably, temporarily permeabilizes the skin so that once the neurotoxin has been delivered through the skin, the skin reduces its permeability to other factors.

In one embodiment of the invention, the enhancing agent is an alcohol. Examples of alcohols include short chain alcohols, such as alcohols having between about 2-5 carbon atoms. Some short chain alcohols include ethanol, isopropanol, methanol, and isobutanol, or combinations thereof. The alcohols may be mixed in the composition so that the concentration of alcohol in the composition is between about 10% and 40%. The alcohol may be admixed with glycerin to reduce potential irritation caused by higher concentrations of alcohol. Long chain alcohols are also useful to enhance the transdermal administration of neurotoxins, such as botulinum toxins. Examples of long-chain alcohols include alcohols having between about 8 and 12 carbon atoms, and some specific examples include n-dodekano, klenbuterol, and albuterol. Polyalcohols may also be used with the neurotoxin. Examples include propylene glycol, glycerol, polyethylene glycol, and dexpantheol, and combinations thereof.

In another embodiment, an enhancing agent may be a vesicle that is able to store the neurotoxin within the vesicle. The vesicle can diffuse through the skin and thereby deliver the neurotoxin to the target site. The vesicle may be a lipid vesicle. In one specific embodiment, the neurotoxin is incorporated into a transfersome, which are deformable carries containing lipids and membrane softeners (e.g., Hofer et al., *New Ultradeformable Drug Carriers for Potential Transdermal Application of Interleukin-2 and Interferon-α: Theoretic and Practical Aspects*, World J. Surg. 24, 1187-1189 (2000); and U.S. Pat. No. 6,165,500). Surprisingly, it has been discovered that transfersomes sufficiently transport neurotoxins, including botulinum toxin complexes, across the skin to achieve a therapeutic effect. In other words, the neurotoxin is able to be delivered to a target site and still be bioactive after diffusing through the skin.

The compositions of the invention may be used in an application device that permits application of the composition to a target site on the skin without applying the composition to non-target site areas of the skin. For example, a device may be employed that allows the composition to be applied without first applying the composition to one's fingers, which may lead to undesirable paralysis of the fingers. Suitable devices include spatulas, swabs, syringes without needles, and adhesive patches. Use of spatulas or swabs, or the like may require the device to be inserted into a container containing the composition. Using syringes or adhesive patches may be accomplished by filling the syringe or patch with the composition. The composition may then be topically spread by the spatulas or swabs, or may be expelled from the syringes onto the person's skin.

In one embodiment of the invention, the composition containing the neurotoxin and the enhancing agent is provided in an adhesive patch. Some examples of adhesive patches are well known. For example, see U.S. Pat. Nos. Des. 296,006; 6,010,715; 5,591,767; 5,008,110; 5,683,712; 5,948,433; and 5,965,154. Transdermal patches are generally characterized as having an adhesive layer, which will be applied to a person's skin, a depot or reservoir for holding a pharmaceutical agent, and an exterior surface that prevents leakage of the pharmaceutical from the depot. The exterior surface of a patch is typically non-adhesive.

In accordance with the present invention, the neurotoxin is incorporated into the patch so that the neurotoxin remains stable for extended periods of time. The neurotoxin may be incorporated into a polymeric matrix that stabilizes the neurotoxin, and permits the neurotoxin to diffuse from the matrix and the patch. The neurotoxin may also be incorporated into the adhesive layer of the patch so that once the patch is applied to the skin, the neurotoxin may diffuse through the skin. In accordance with such an embodiment, the adhesive preferably comprises an enhancing agent, as disclosed herein. In one embodiment, the adhesive layer may be heat activated where temperatures of about 37 degrees Celsius cause the adhesive to slowly liquefy so that the neurotoxin diffuses through the skin. The adhesive may remain tacky when stored at less than 37 degrees Celsius, and once applied to the skin, the adhesive loses its tackiness as it liquefies. The administration of the toxin is complete once the patch no longer adheres to the skin.

Alternatively, the neurotoxin may be provided in one or more wells or pockets disposed near the surface of the patch that will contact the skin. In one embodiment, the neurotoxin is stored in the wells in a dried, or lyophilized state. Storing such patches in a cooled atmosphere (e.g., about 4 degrees Celsius) maintains the stability of the neurotoxin. A patch may be removed from the cool atmosphere when needed, and applied to a person's skin where the neurotoxin may be solubilized upon the mixing with fluid, such as water or saline. The fluid may be provided separately or as a component of the patch. For example, fluid may be provided on a person's skin so that when the patch containing the dried neurotoxin interacts with the fluid, the neurotoxin is exposed to the fluid and is solubilized. The solubilized neurotoxin may then be able to be absorbed by the skin. As another example, the patch may contain one or more wells or pockets to hold fluid in the patch. The fluid may be forced from the wells or pockets to cause the fluid to mix with the dried neurotoxin. In such embodiments, the enhancing agent may be provided in the fluid to enhance the permeability of the skin to the neurotoxin. For example, the fluid may be provided in a pocket in the patch. Pressure exerted on the patch causes the pocket to rupture and release the fluid so that it mixes with the dried neurotoxin. The composition containing the neurotoxin may thus diffuse through the patient's skin. As another example, fluid, including gels and creams containing water may be applied to the skin at a target site. The patch containing the dried neurotoxin may then be applied to the skin where the fluid mixes with the neurotoxin and the composition diffuses into the skin.

In patches containing wells of dried neurotoxin, it is desirable to seal the wells so that the neurotoxin remains in the wells until the neurotoxin is to be administered. Accordingly, the wells are sealed with a membrane or film that prevents the neurotoxin from diffusing from the wells in the neurotoxin's dry state, but that permits the neurotoxin to diffuse from the wells when it is solubilized. The membrane may either be porous or nonporous. In one embodiment, the membrane comprises cellulose or starch, and more particularly, the membrane may contain polyvinyl alcohol, polyethylene oxide, and hydroxypropyl methyl cellulose. The membrane is thin (ranging in thickness from about 1 μm to about 1 mm) and dissolves upon contacting fluid. Thus, fluid placed on the person's skin or fluid directed from a pocket in the patch may contact the cellulose membrane and cause the membrane to dissolve. After dissolving, the fluid mixes with the dried neurotoxin and solubilizes the neurotoxin. The composition then diffuses through the patient's skin.

Additionally, the transdermal patch may include a plurality of small needles that extend through the stratum corneum, but do not extend into the dermis to rupture blood vessels. The needles may be between 20 µm and 1 mm long when extending from the dermal surface of the patch. Thus, the needles extend through the stratum corneum, but terminate before the dermis where the capillary beds are located. The needles may be solid or hollow. Hollow needles may have a lumen extending along their length so that the composition can pass from the depot in the patch to the end of the needle in the epidermis. Solid needles may be used to permit the composition to diffuse along the outer surface of the needle into the epidermis. Surprisingly, it has been discovered that this length of needles is optimal to reduce potential pain caused by longer needles activating sensory pain fibers. Thus, the composition containing the neurotoxin may be applied subdermally without significant, if any, pain to the patient.

Accordingly, methods of inhibiting neurotransmitter release in subdermal structures may include steps of disrupting the stratum corneum to reduce the impermeability of the stratum corneum, and applying a botulinum toxin to the skin location in which the stratum corneum has been disrupted. Disrupting the stratum corneum refers to either completely removing the stratum corneum from a region of a patient's skin, or partially removing portions of the stratum corneum at a location on the patient's skin so that relatively small stratum corneum-free regions of skin are present. The skin may be disrupted using any suitable method without imparting significant pain to the patient. In preferred embodiments of the methods, the stratum corneum is non-chemically disrupted. For example, the stratum corneum may be abrasively scrubbed to disrupt the laminar barrier of the stratum corneum. Or, the stratum corneum may be disrupted by applying an adhesive, such as adhesive tape or wax, to the skin, and subsequently removing the adhesive from the skin. Because such methods of disrupting the stratum corneum may cause some pain, it may be desirable to provide a topical anesthetic to the skin, such as lidocaine cream, to temporarily reduce any pain that may be caused by the disruption.

Additional transdermal methods that non-chemically enhance the skin's permeability include low frequency ultrasound (20 kHz to 1 MHz). Ultrasound is defined as sound at a frequency of between about 20 kHz and 10 MHz, with intensities of between 0 and 3 W/cm$^2$. Low frequency ultrasound, as used herein, refers to ultrasound at a frequency that is less than 1 MHz, and preferably in the range of 20 kHz to 40 kHz. The ultrasound is delivered in pulses, for example, 100 msec pulses at a frequency of 1 Hz. The intensity of the ultrasound may vary between 0 and 1 W/cm$^2$, and frequently varies between 12.5 mW/cm$^2$ and 225 mW/cm$^2$. Typical duration of exposure to ultrasound is between about 1 and about 10 minutes. The ultrasound is applied without causing an increase in skin temperature greater than about 1 degree Celsius. Low frequency ultrasound may be used alone or in combination with the composition to improve the permeability of the skin to the neurotoxin. Examples of ultrasound techniques for improving skin permeability may be found in U.S. Pat. Nos. 6,002,961 and 5,814,599. Surprisingly, it has been discovered that low frequency ultrasound, when applied in conjunction with a composition containing a botulinum toxin, permeabilizes the skin but does not substantially alter the three dimensional conformation of the neurotoxin, such as purified botulinum toxin or botulinum toxin complexes. Thus, the bioactivity of the neurotoxin is maintained and the disorder is substantially treated.

Additionally, the ultrasound may be delivered prior to application of the botulinum toxin to the skin. It has been discovered that low frequency ultrasound when applied before the topical application of botulinum toxin, temporarily disrupts the stratum corneum so that subsequent topical application of botulinum toxin achieves a therapeutic effect. In other words, the disruption caused by the ultrasound persists for several minutes, for example between about 10 and 30 minutes, to provide relatively easy transdermal delivery of botulinum toxin to the patient. After about 30 minutes, the stratum corneum begins to resume its natural structure, and the permeability of the stratum corneum temporally decreases. Thus, one method of the invention, includes the step of applying low frequency ultrasound to one or more regions of the skin, and subsequently topically applying botulinum toxin to those regions of the skin that were exposed to the low frequency ultrasound, where the botulinum toxin is provided in a composition containing an enhancing agent, which facilitates prolonged penetration of the botulinum toxin to the patient.

Additional approaches include iontophoresis which can help deliver the botulinum toxin to a subdermal target site by passing electrical current across a patch containing a composition comprising botulinum toxin. In one embodiment, an electrode may be applied on the external surface of the transdermal patch, and a ground electrode is provided elsewhere on a patient's skin. Small direct current is applied through the electrode positioned on the transdermal patch to urge the botulinum toxin in the composition through the patient's skin. The amount of current is typically less than 1 mA/cm$^2$, and in a preferred embodiment, the current is applied in an amount between 0.3 mA/cm$^2$ and 0.7 mA/cm$^2$. Because the effectiveness of transdermal delivery of the botulinum toxin through the skin is at least partially dependent on the polarity of the botulinum toxin, it may be desirable to increase the acidity of the composition to lower the pH of the composition and impart a charge on the botulinum toxin to facilitate the effectiveness of the electrical current in transporting the toxin through the skin. The pH of the composition containing the botulinum toxin can be lowered to as low as 4 without significantly compromising the bioactivity of the molecule; however, preferred pH ranges are between 5.5 and 7.2. Additionally, the current is passed through the electrodes for a time that does not permanently damage (e.g., burn) the skin. For example, the current may be passed for a period of time between about 1 minute and 15 minutes. For longer applications, it is desirable to pulse the current to reduce potentially damaging effects caused by the electricity.

The neurotoxin may be topically administered by any suitable method as determined by the attending physician. The methods of administration permit the neurotoxin to be administered locally to a selected target tissue. Methods of administration include coating the skin with the composition so that the composition covers at least a portion of the target site. Administration methods also include applying a transdermal patch to the target site of the skin and causing the neurotoxin in the transdermal patch to diffuse into the skin. For extended applications, adhesive patches are utilized so that the composition can slowly diffuse into the skin without repeated applications of the patch. For example, a patch may include a microprocessor that provides periodic release of neurotoxin from the patch. Microprocessor patches may be especially advantageous in patches that have the microneedles or low frequency ultrasound devices, as discussed above. The microprocessor can provide a timed release of the composition depending on the particular condition being treated. An example of a microprocessor controlled pharmaceutical treatment device may be found in U.S. Pat. No. 6,334,856.

Diffusion of biological activity of a botulinum toxin within a tissue appears to be a function of dose and can be graduated. Jankovic J., et al *Therapy With Botulinum Toxin*, Marcel Dekker, Inc., (1994), page 150. Thus, diffusion of botulinum toxin can be controlled to reduce potentially undesirable side effects that may affect the patient's disorder. For example, the neurotoxin may be administered so that the neurotoxin primarily effects sensory neurons involved in inflammation, and does not affect other subdermal targets. In such a case, the composition may be applied for a relatively short period of time (e.g., 1-4 hours) to permit only local diffusion into the dermis of the patient where the sensory neurons terminate. The neurotoxin may thus act on the sensory neurons to decrease the release of substance P or CGRP to reduce inflammation and pain associated with inflammation.

Without wishing to be bound by any particular theory, a mechanism can be proposed for the therapeutic effects achieved with the composition practiced according to the present invention. The enhancing agents disclosed herein appear to solubilize the stratum corneum of the epidermis and increase the fluidity of the neurotoxin thus maintaining the bioactivity of the neurotoxin when it reaches the subdermal target. Importantly, the compositions and methods herein of topically administering the neurotoxin permit the neurotoxin to be administered to a patient without resulting in systemic toxicity. As indicated herein, prior art approaches of transdermally administering non-botulinum toxin therapeutic agents have addressed systemic administration of the therapeutic agents via the skin. In addition, prior art approaches for topically applying botulinum toxin to patients have not included the use of enhancing agents, as disclosed herein.

As set forth above, I have discovered that compositions containing a neurotoxin and an enhancing agent surprisingly provides effective and long lasting treatment of disorders associated with neuronal activity near a patient's skin, and reduces the symptoms associated with the disorder. In its most preferred embodiment, the present invention is practiced by topical administration of botulinum toxin type A.

EXAMPLES

The following examples set forth specific compositions and methods encompassed by the present invention to treat patients, and are not intended to limit the scope of the invention. For example, although the following examples are directed to compositions containing botulinum toxin type A, I have discovered that botulinum toxin types B, C, D, E, F, and G are equally effective in being transdermally administered in the compositions set forth herein. It is noted that the dosages of the particular type of botulinum toxin may be adjusted as needed from the particular dosages disclosed herein, as understood by persons of ordinary skill in the art. As indicated above, the transdermal administration methods disclosed herein permit a relatively broad range of concentrations of botulinum toxin without risking the patient's health.

Example 1

One hundred units of botulinum toxin type A are dissolved in 1 mL of water are mixed with 1 mL of 90% ethanol and 1 mL of polyethylene glycol. A syringe is filled with the composition of the botulinum toxin. The viscous solution is expelled from the syringe onto a patient's palm who is complaining of sweaty palms. The solution is spread with a spatula over the entire palmar surface. The patient's hand is covered with a plastic bag with an airtight seal for about one hour to reduce the rate of evaporation of the composition. The bag is removed and the patient washes his hand. Approximately 2 days later, the patient notices that the hand receiving treatment no longer is sweaty while the untreated hand remains sweaty. The reduction in sweat is maintained for about 6 weeks, and then gradually returns. The procedure is repeated for both hands, and both hands show a marked reduction in sweating after a period of about 2 days.

Example 2

A 1 mL 10% suspension of transfersomes is made from 85.8 mg natural phosphatidyl choline and 14.2 mg sodium cholate. Approximately 0.9 mL of phosphate buffer is added to solubilize the lipids. The suspension is filtered several times to achieve a suspension of approximately uniform sized vesicles. Approximately 1000 units of botulinum toxin type A (BOTOX®) are added to the vesicles and are stored at 4 degrees Celsius for at least two days and up to about 30 days.

A patient with brow furrows requests botulinum toxin to reduce the wrinkles. The patient is asked to lay down. A suspension of BOTOX® and transfersomes as described above is topically applied to the patient's forehead. After about 1 hour, the suspension has evaporated. The patient is instructed to wash his face approximately 6 hours later. In about 2-3 days, the patient begins to notice that the forehead wrinkles are reduced in number. At about 7 days, the wrinkles are gone. The effects of the BOTOX® last for about 4 months.

Example 3

Lyophilized BOTOX® is provided in a plurality of wells located on a dermal side of a transdermal adhesive patch. The transdermal patch has dimensions of approximately two inches by three inches (5 cm×7.5 cm). The wells are organized in grids of approximately 1 cm$^2$ on the dermal side of the patch (i.e., the side of the patch that will be adjacent the skin). Each grid contains approximately 100 wells. The dermal side of the patch is fabricated from polyethylene terephthalate (PET). Each well contains between about 50-100 units of lyophilized BOTOX. The wells are sealed with a dissolvable membrane film made of polyvinyl alcohol, polyethylene oxide, and hydroxypropyl methyl cellulose. An adhesive border is provided around the grid. The adhesive border is approximately 1 cm wide and comprises a rubber adhesive, such as R-1072 from B.F. Goodrich Co. A patch containing the lyophilized BOTOX in a plurality of wells may be stored at 4 degrees Celsius for several months without affecting the bioactivity of the toxin.

Two patches, as described above, are applied to the skin of a patient's lower back on either side of the spinal cord at a location demonstrating extreme muscle hyperactivity. Prior to application, the skin is prepared by cleaning the site with 95% ethanol. A gel containing water, 80% ethanol, and polyethylene glycol is applied in an area about one inch by two inches on either side of the spinal cord. Each patch is adhesively applied to the back where the gel is located. The patch is left in place for 5-7 days. The gel dissolves the membrane and solubilizes the botulinum toxin in the wells. After about 4 days, the patient notices relaxation of his lower back muscles, and a reduction in pain associated with the muscle contractions. By 7 days, the patient indicates the pain is completely gone. The pain relieving effect persists for about 5 months.

Example 4

A patient with cervical dystonia receives four transdermal patches, each having dimensions of approximately 2 inches by 3 inches, applied to the skin overlying the rigid muscles. The transdermal patches contain a depot of dried BOTOX®, and a pocket of saline. An ultrasound device is applied over the patch. Ultrasound is applied to the patch and the patient's skin at a frequency of 15 kHz for a period of 10 minutes. The ultrasound energy is pulsed to reduce damaging the patient's skin. After 10 minutes, the physician removes the ultrasound device, and applies pressure to the transdermal patches to cause the pocket of saline to rupture. The saline that is expelled from the pocket mixes with the botulinum toxin to solubilize the toxin. The composition is delivered through the skin by diffusion. The patches are left in place for about 5 hours. Approximately 2-3 days after the treatment, the patient experiences some relief of pain and relaxation of the muscles. Approximately 7 days after treatment, the pain is almost completely relieved. The therapeutic effects persist for about 3 months.

Example 5

A patient with suffering from palmar hyperhydrosis requests botulinum toxin therapy. The physician evaluates the patient and determines that the patient is a reasonable candidate for botulinum toxin therapy. The physician abrasively scrubs the patient's palms with a pumice stone. After the majority of the skin has been roughened, the physician applies a saline based gel containing approximately 10 units of BOTOX® to the patient's palm. The patient's hands are kept in plastic bags that have been sealed around the patient's wrists to prevent rapid evaporation of the gel. The patient's hands are left in the bags for about 4 hours. About 2 days after treatment, the patient notices a reduction in the hyperhydrosis of his palms. By 7 days, the sweating is completely eliminated, and the patient does not report any appreciable loss of muscle activity. The hyperhydrosis alleviating effects persist for about six to eight weeks.

Example 6

A transdermal patch containing approximately 1000 units of BOTOX® is applied to a patient's inflamed elbow after the skin of the elbow has been prepared by abrasively scrubbing the skin with a pumice stone. After scrubbing the skin, a gel is applied to the elbow before the transdermal patch is applied. The patch is applied to the elbow in a flexed position. The gel dissolves the cellulose membrane of the patch and solubilizes the botulinum toxin contained therein. About 1 hour after the patch is applied to the elbow, enough time for the membrane to dissolve and the toxin to be solubilized, an electrode is placed on the outer surface of the patch. A ground electrode is attached to the patient's torso. Current is passed through the electrode at an intensity of 0.5 mA/cm$^2$ for 5 minutes. After resting for 2 minutes, current is again passed through the electrode for 5 minutes. The patient leaves the physician's office, and is asked to leave the patch in place for about 4 days. After about 2 days, the patient notices a reduction of inflammation accompanied by a reduction in pain. By about 7 days, the pain is almost completely alleviated. The relief provided by the botulinum toxin persists for about 4 months.

Transdermal compositions containing botulinum toxin and methods of administering such compositions according to the invention disclosed herein have many benefits and advantages, including the following:

1. the symptoms, such as the symptoms associated with hyperactive neuronal systems associated with spastic muscles, inflammation, or hyperhydrosis can be dramatically reduced.
2. the symptoms can be reduced for from about two to about five months per application of neurotoxin to the skin and for from about one year to about five years upon use of slow release compositions and patches.
3. the administered neurotoxin shows little or no tendency to diffuse or to be transported away from subdermal site.
4. few or no significant undesirable side effects occur from topical administration of the neurotoxin.
5. the suppressant effects of the compositions can result in the desirable side effects of greater patient mobility, a more positive attitude, and an improved quality of life.
6. high, therapeutic doses of a neurotoxin can be delivered to subdermal target tissue over a prolonged period without systemic toxicity.

Although the present invention has been described in detail with regard to certain preferred methods, other embodiments, versions, and modifications within the scope of the present invention are possible. For example, a wide variety of neurotoxins can be effectively used in the compositions and methods of the present invention.

All references, articles, patents, applications and publications set forth above are incorporated herein by reference in their entireties.

Accordingly, the spirit and scope of the following claims should not be limited to the descriptions of the preferred embodiments set forth above.

I claim:

1. A method of relieving pain in a patient caused by a spastic muscle, the method comprising the steps of:
   (a) applying ultrasound at a frequency between about 10 kHz and 1 MHz to the patient's skin overlying the spastic muscle; and
   (b) applying a botulinum toxin, incorporated into an adhesive layer of a transdermal patch, to the patient's skin that has received the ultrasound in step (a), where the adhesive layer is heat activated such that at a temperature of about 37 degrees Celsius the adhesive layer slowly liquefies;
   wherein said botulinum toxin has a molecular weight of about 150 kD or more and said method does not result in significant amounts of botulinum toxin passing into the circulatory system.

2. The method of claim 1, further comprising a step of abrasively removing a portion of the stratum corneum of the patient's skin that received the ultrasound.

3. The method of claim 1, wherein the botulinum toxin is botulinum toxin type A.

4. The method of claim 1, wherein the botulinum toxin is administered in a composition comprising an enhancing agent that facilitates penetration of the botulinum toxin through the patient's skin.

5. The method of claim 1, wherein the botulinum toxin is selected from the group consisting of the botulinum toxins types A, B, C, D, E, F and G.

6. The method of claim 2, wherein the stratum corneum is abrasively removed by applying an adhesive to a skin and subsequently removing the adhesive from the skin.

7. The method of claim 4, wherein the enhancing agent is an alcohol.

8. The method of claim 7, wherein the concentration of the alcohol in the composition is between about 10% and about 40%.

9. The method of claim 7 wherein the enhancing agent further comprises a glycerin.

10. The method of claim 4, wherein the enhancing agent is a vesicle that is able to store the botulinum toxin.

11. The method of claim 10, wherein the vesicle is a lipid vesicle.

12. The method of claim 10, wherein the vesicle is a transfersome.

13. The method of claim 1, wherein the botulinum toxin is incorporated into a polymeric matrix.

14. A method of relieving pain in a patient caused by a spastic muscle, the method comprising the steps of:
　(a) applying ultrasound at a frequency between about 10 kHz and 1 MHz to the patient's skin overlying the spastic muscle;
　(b) abrasively removing a portion of a stratum corneum of the patient's skin that received the ultrasound in step (a); and
　(c) applying a botulinum toxin type A to the patient's skin that has received the ultrasound in step (a);
　wherein the botulinum toxin type A has a molecular weight of about 150 kD or more and is applied in an adhesive layer of a heat activated transdermal patch applied to the patient's skin, the adhesive layer further comprising an alcohol and a glycerin; wherein the adhesive layer slowly liquefies at a temperature of about 37 degrees Celsius and wherein said method does not result in significant amounts of botulinum toxin passing into the circulatory system.

* * * * *

UNITED STATES PATENT AND TRADEMARK OFFICE
CERTIFICATE OF CORRECTION

PATENT NO.         : 7,704,524 B2                                                           Page 1 of 2
APPLICATION NO. : 11/159511
DATED              : April 27, 2010
INVENTOR(S)        : Stephen Donovan It is certified that error appears in the above-identified patent and that said Letters Patent is hereby corrected as shown below:

In column 3, line 21, delete "hemaglutinin" and insert -- hemagglutinin --, therefor.

In column 3, line 22, delete "nonhemaglutinin" and insert -- nonhemagglutinin --, therefor.

In column 4, line 33, delete "proteins" and insert -- proteins, --, therefor.

In column 6, line 24, delete "S 10." and insert -- S10. --, therefor.

In column 6, line 63, delete "riot" and insert -- not --, therefor.

In column 7, line 10, delete "comeum," and insert -- corneum, --, therefor.

In column 7, line 12, delete "comeum" and insert -- corneum --, therefor.

In column 7, line 15, delete "comeum" and insert -- corneum --, therefor.

In column 7, line 23, delete "comeum" and insert -- corneum --, therefor.

In column 7, line 47, delete "comeum." and insert -- corneum. --, therefor.

In column 7, line 54, delete "comeum." and insert -- corneum. --, therefor.

In column 7, line 66, delete "46 kD," and insert -- 48 kD, --, therefor.

In column 8, line 61, delete "to;" and insert -- to, --, therefor.

In column 9, line 65, delete "comeum" and insert -- corneum --, therefor.

In column 10, line 61, delete "comeum" and insert -- corneum --, therefor.

In column 10, line 65, delete "comeum." and insert -- corneum. --, therefor.

In column 11, line 7, delete "comeum" and insert -- corneum --, therefor.

In column 11, line 8, delete "comeum;" and insert -- corneum; --, therefor.

In column 11, line 10, delete "comeum" and insert -- corneum --, therefor.

In column 11, line 11, delete "comeum" and insert -- corneum --, therefor.

In column 11, line 12, delete "comeum." and insert -- corneum. --, therefor.

Signed and Sealed this

Thirty-first Day of August, 2010

David J. Kappos
*Director of the United States Patent and Trademark Office*

CERTIFICATE OF CORRECTION (continued)
U.S. Pat. No. 7,704,524 B2

In column 11, line 12, delete "comeum" and insert -- corneum --, therefor.

In column 11, line 15, delete "comeum" and insert -- corneum --, therefor.

In column 11, line 18, delete "comeum" and insert -- corneum --, therefor.

In column 11, line 21, delete "comeum" and insert -- corneum --, therefor.

In column 11, line 36, delete "comeum" and insert -- corneum --, therefor.

In column 11, line 62, delete "dystonia;" and insert -- dystonia, --, therefor.

In column 13, line 6, delete "anent" and insert -- agent --, therefor.

In column 13, line 29, delete "dexpantheol," and insert -- dexpanthenol, --, therefor.

In column 15, line 4, delete "comeum," and insert -- corneum, --, therefor.

In column 15, line 8, delete "comeum," and insert -- corneum, --, therefor.

In column 15, line 22, delete "comeum" and insert -- corneum --, therefor.

In column 15, line 23, delete "comeum," and insert -- corneum, --, therefor.

In column 15, line 24, delete "comeum" and insert -- corneum --, therefor.

In column 15, line 25, delete "comeum" and insert -- corneum --, therefor.

In column 15, line 26, delete "comeum" and insert -- corneum --, therefor.

In column 15, line 27, delete "comeum" and insert -- corneum --, therefor.

In column 15, line 29, delete "comeum" and insert -- corneum --, therefor.

In column 15, line 32, delete "comeum" and insert -- corneum --, therefor.

In column 15, line 33, delete "comeum" and insert -- corneum --, therefor.

In column 15, line 35, delete "comeum." and insert -- corneum. --, therefor.

In column 15, line 35, delete "comeum" and insert -- corneum --, therefor.

In column 15, line 38, delete "comeum" and insert -- corneum --, therefor.

In column 16, line 5, delete "comeum" and insert -- corneum --, therefor.

In column 16, line 11, delete "comeum" and insert -- corneum --, therefor.

In column 16, line 12, delete "comeum" and insert -- corneum --, therefor.

In column 17, line 22, delete "comeum" and insert -- corneum --, therefor.

In column 20, line 52, in claim 2, delete "comeum" and insert -- corneum --, therefor.

In column 20, line 63, in claim 6, delete "comeum" and insert -- corneum --, therefor.

In column 22, line 1, in claim 14, delete "comeum" and insert -- corneum --, therefor.